United States Patent
Demmer et al.

(10) Patent No.: US 9,056,003 B2
(45) Date of Patent: Jun. 16, 2015

(54) TISSUE GRAFT FIXATION

(71) Applicants: Matthew Demmer, Memphis, TN (US);
Stephen Anthony Santangelo,
Sturbridge, MA (US); Konsei Shino,
Osaka (JP)

(72) Inventors: Matthew Demmer, Memphis, TN (US);
Stephen Anthony Santangelo,
Sturbridge, MA (US); Konsei Shino,
Osaka (JP)

(73) Assignee: Smith & Nephew, Inc., Memphis, TN (US)

( * ) Notice: Subject to any disclaimer, the term of this patent is extended or adjusted under 35 U.S.C. 154(b) by 47 days.

(21) Appl. No.: 13/750,311

(22) Filed: Jan. 25, 2013

(65) Prior Publication Data

US 2014/0214163 A1    Jul. 31, 2014

(51) Int. Cl.
*A61F 2/08*        (2006.01)
*A61B 17/04*       (2006.01)

(52) U.S. Cl.
CPC ............ *A61F 2/0811* (2013.01); *A61B 17/0401* (2013.01); *A61B 2017/0459* (2013.01); *A61B 2017/0417* (2013.01)

(58) Field of Classification Search
USPC ............................ 623/13.11–17.11; 606/232
See application file for complete search history.

(56) References Cited

U.S. PATENT DOCUMENTS

| | | | |
|---|---|---|---|
| 4,633,862 A | 1/1987 | Petersen | |
| 5,282,866 A | 2/1994 | Cohen et al. | |
| 5,306,301 A | 4/1994 | Graf et al. | |
| 5,527,341 A | 6/1996 | Gogolewski et al. | |
| 6,117,161 A * | 9/2000 | Li et al. | 606/232 |
| 6,364,884 B1 * | 4/2002 | Bowman et al. | 606/916 |
| 6,402,766 B2 * | 6/2002 | Bowman et al. | 606/151 |
| 7,651,528 B2 * | 1/2010 | Montgomery et al. | 623/13.14 |
| 2002/0161439 A1 | 10/2002 | Strobel et al. | |
| 2003/0055509 A1 | 3/2003 | McCue et al. | |
| 2005/0288709 A1 | 12/2005 | Fallin et al. | |
| 2008/0027441 A1 | 1/2008 | Lopez et al. | |
| 2009/0204146 A1 | 8/2009 | Kaiser et al. | |
| 2009/0306783 A1 | 12/2009 | Blum | |
| 2010/0125297 A1 | 5/2010 | Guederian et al. | |
| 2010/0255444 A1 * | 10/2010 | Karmon | 433/172 |
| 2011/0009866 A1 * | 1/2011 | Johnson et al. | 606/70 |
| 2013/0304120 A1 * | 11/2013 | Stone et al. | 606/232 |
| 2014/0155937 A1 | 6/2014 | Shinde | |

FOREIGN PATENT DOCUMENTS

| | | |
|---|---|---|
| CN | 201040016 Y | 3/2008 |
| WO | 2007073563 A2 | 6/2007 |
| WO | 2012052891 A1 | 4/2012 |
| WO | WO2012129617 A1 | 10/2012 |

OTHER PUBLICATIONS

International Search Report, PCT/US2014/012445.

* cited by examiner

*Primary Examiner* — Suzette J Gherbi
(74) *Attorney, Agent, or Firm* — Chapin IP Law, LLC

(57) ABSTRACT

A tissue graft fixation device including a body having an upper and lower surface, a first end portion, a second end portion, and an intermediate portion extending between the first and second end portions, the intermediate portion comprising at least two tabs extending transverse to the intermediate portion, the intermediate portion defining at least one hole located between the at least two tabs, and each of the at least two tabs comprising a keel extending transverse to the intermediate portion and including a cutting edge.

13 Claims, 4 Drawing Sheets

TISSUE GRAFT FIXATION

TECHNICAL FIELD

The present disclosure relates to tissue graft fixation.

BACKGROUND

A ligament, such as an anterior cruciate ligament (ACL), that has ruptured and is non-repairable, is generally replaced arthroscopically by a tissue graft. The tissue graft can be harvested from a portion of a patellar tendon having so called "bone blocks" at each end, and from the semitendinosus and gracilis. Alternatively, the tissue graft can be formed from synthetic materials or from a combination of synthetic and natural materials.

The replacement tissue graft is implanted by securing one end of the tissue graft in a socket formed in a passage within the femur, and passing the other end of the graft through a passage formed in the tibia. Generally, sutures are used to affix each end of the tissue graft to a fastener (e.g., an interference screw or a post), which is then secured to the bone.

It is also known to use a graft fixation member, e.g., a fixation button, to secure the tissue graft at the femoral cortex, as described in U.S. Pat. No. 5,306,301 ("the '301 patent") hereby incorporated by reference in its entirety. The graft fixation member is coupled to the tissue graft and a suture, or other pulling means, is used to pull the fixation member/tissue graft combination through the bone tunnel. However, these fixation members can be cumbersome to use, due to the hole and suture loop placements on the member making it difficult to pass the graft through the tunnel. In addition, the member comes in various sizes, which makes it difficult to center the member on the top opening of the femoral tunnel. Furthermore, as the member is being drawn through the bone tunnel, the member frequently rotates off-axis, rather than maintaining a generally longitudinal orientation.

SUMMARY

In one general aspect, a tissue graft fixation device includes a body having an upper and lower surface, a first end portion, a second end portion, and an intermediate portion extending between the first and second end portions, the intermediate portion comprising at least two tabs extending transverse to the intermediate portion, the intermediate portion defining at least one hole located between the at least two tabs, and each of the at least two tabs comprising a keel extending transverse to the intermediate portion and including a cutting edge.

Implementations may include one or more of the following features. For example, the cutting edge of each keel of the at least two tabs is tapered at an angle relative to the lower surface of the body of the fixation device. The first end portion defines at least one hole and the second end portion defines at least one hole. Each of the at least two tabs includes a pair of keels extending transverse to the intermediate portion, and each of the keels comprises a cutting edge. The cutting edge of each of the keels is tapered at an angle relative to the lower surface of the body of the fixation device. The intermediate portion defines at least two holes located between the at least two tabs. The at least two tabs are disposed along opposite outer edges of the intermediate portion of the device.

In another general aspect, a tissue graft fixation device includes a body having a first end portion, a second end portion, and an intermediate portion extending between the first and second end portions, the body configured for passage through a bone tunnel when oriented generally longitudinally with respect to the bone tunnel, the intermediate portion comprising two tabs extending transverse to the intermediate portion and the intermediate portion defining at least one hole located between the two tabs, the two tabs configured to at least partially fit through an opening and into the bone tunnel to limit translation of the device on a cortical bone surface, and each of the two tabs comprising two axially extending and tapered keels, each of the keels comprising a cutting edge configured to drive into a portion of the cortical bone surface to limit rotation of the device.

Implementations may include one or more of the following features. For example, the cutting edge of each keel is tapered at an angle relative to a lower surface of the body of the fixation device. The first end portion defines at least one hole and the second end portion defines at least one hole. The intermediate portion defines at least two holes located between the two tabs. The two tabs are disposed along opposite outer edges of the intermediate portion of the device.

In another general aspect, a method includes looping a tissue graft through an opening in a tissue graft fixation device, and pulling the tissue graft fixation device and looped graft through a bone tunnel, positioning at least two tabs extending from one side of the fixation device within the bone tunnel to limit translation of the fixation device on a cortical bone surface, and seating cutting edge portions of at least two axially extending and tapered keels integrally formed with the at least two tabs into a portion of the cortical bone surface to limit rotation of the device relative to the cortical bone surface.

Implementations may include one or more of the following features. For example, the fixation device defines a plurality of openings disposed between the two tabs. Pulling the tissue graft fixation device and looped graft through a bone tunnel comprises pulling a loop of a flexible member coupled through an opening defined in one end portion of the fixation device through the bone tunnel. The flexible member includes a suture.

Other features will be apparent from the description and drawings, and from the claims.

It should be understood that the drawings are not necessarily to scale and that the disclosed implementations are sometimes illustrated diagrammatically and in partial views. In certain instances, details which are not necessary for an understanding of the disclosure or which render other details difficult to perceive may have been omitted. It should be understood, of course, that this disclosure is not limited to the particular implementations illustrated herein.

DETAILED DESCRIPTION

Figure 1:
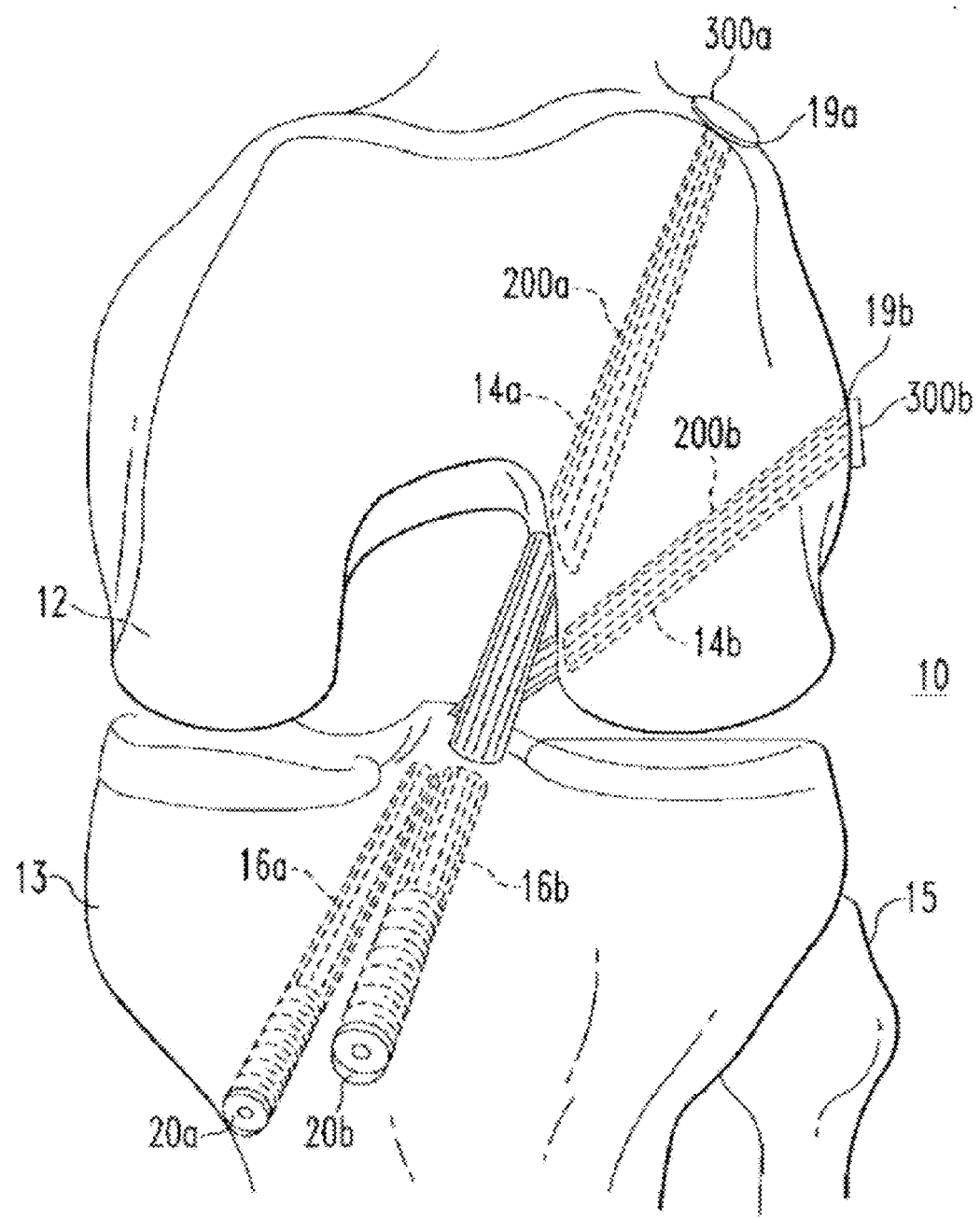
FIG. 1 shows a tissue graft secured within tibia and femoral bone tunnels during an ACL reconstruction procedure.

Referring to FIG. 1, during a multiple-bundle, ligament repair and reconstruction procedure, tissue grafts 200a, 200b are secured at openings 19a, 19b to femoral channels 14a, 14b within a knee 100 using graft fixation members 300a, 300b, respectively. The tissue grafts 200a, 200b are tensioned at opposing ends of the channels 14a, 14b from the fixation member 300a, 300b by a surgeon and secured in place with bone anchors 20a, 20b within tibial channels 16a, 16b.

The use of a multiple-bundle technique, e.g., more than one femoral channel 14, tibial channel 16, tissue graft 200 and fixation member 300, results in a repaired joint that is more anatomically correct than a single bundle technique, e.g., a single femoral channel 14, tissue graft 200 and fixation member 300. The multiple-bundle technique results in multiple anchor points to transfer stresses evenly across the knee joint and/or permits a surgeon to drill femoral and tibial channels that are more laterally oriented, closer to the joint between the tibia 13 and fibula 15, and shallower than bone channels that are typically drilled farther away from the knee joint, and thus deeper. Further, securing the tissue grafts 200a, 200b directly to the fixation members 300a, 300b permits the surgeon to drill shallower bone channels than what may be possible when intermediate suture is used to connect a tissue graft to a fixation member, and due to the larger size of the fixation member as compared to conventional fixation members, such as the Endobutton CL, available from Smith & Nephew, Inc., permits the bone tunnels to have a uniform cross-section that receives both the tissue graft and the fixation member to lie over the larger sized bone tunnel when the fixation member is positioned against the cortex at the opening to the femoral tunnel.

Figure 2A:
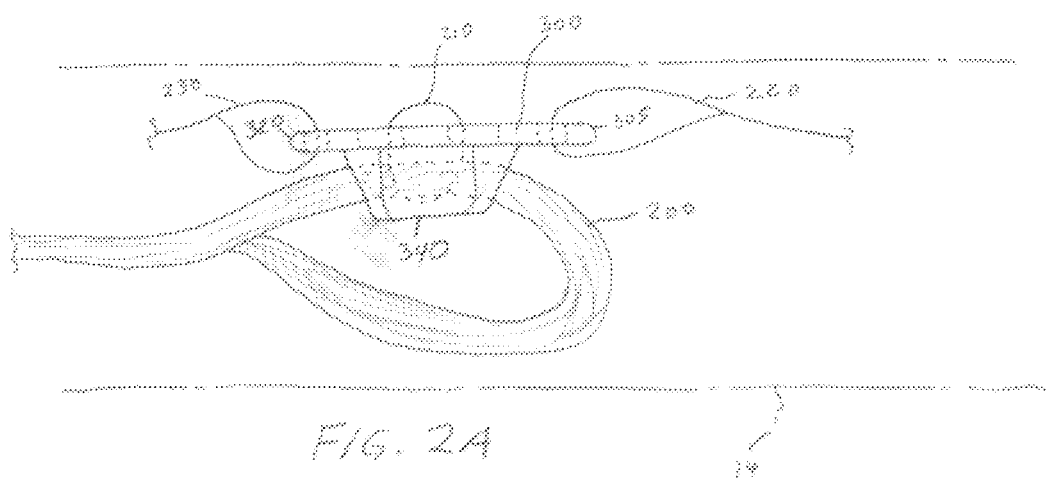
FIG. 2A is a side view of a fixation member shown drawing the tissue graft through the femoral bone tunnel.
Figure 2B:
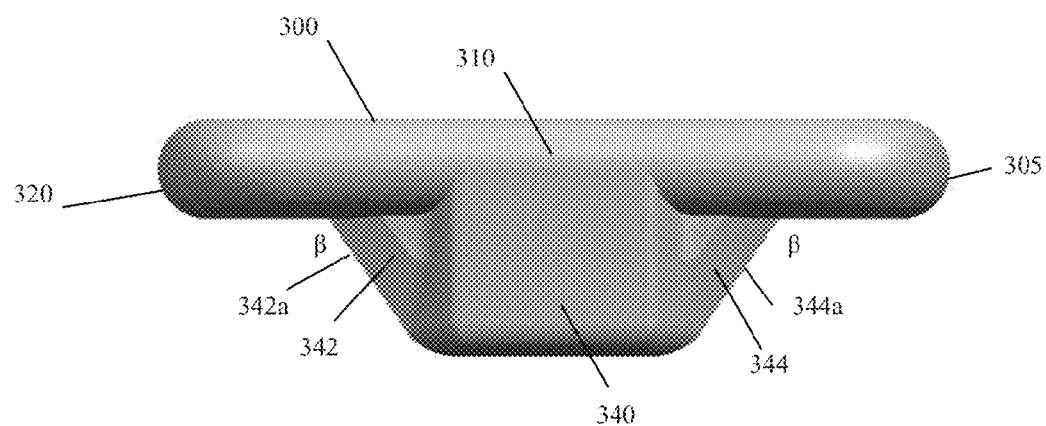
FIG. 2B is a side view of the fixation member of FIG. 2A.
Figure 2C:
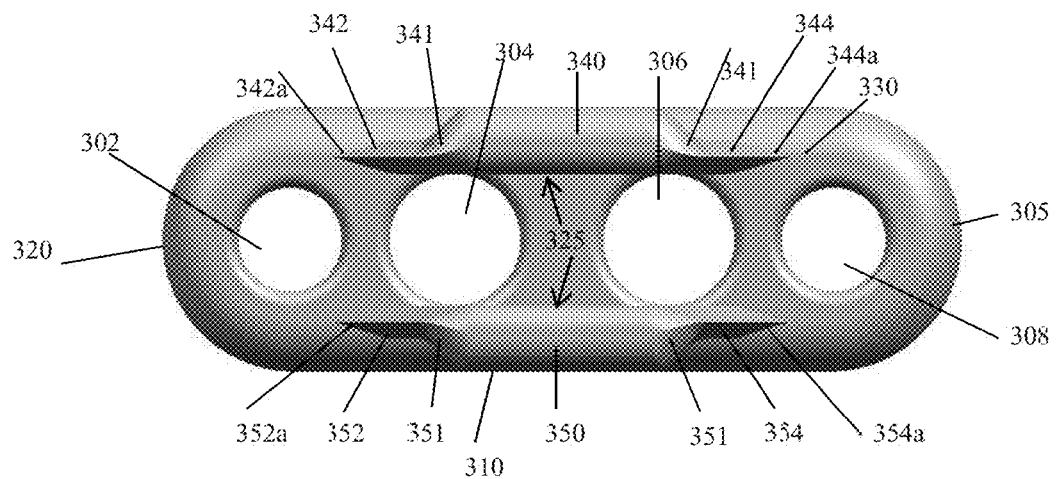
FIG. 2C is a bottom view of the fixation member of FIG. 2A.

As shown in FIGS. 2A-2C, the tissue graft 200 is indirectly coupled to the fixation member 300 via a continuous loop 210 of material passed through central holes 304, 306 formed within an intermediate portion 310 of the fixation member 300. A lead suture 220 is passed through a lead suture hole 308 at a first end portion 305 of the member 300, and a trailing suture 230 is passed through a trailing suture hole 302 at a second end portion 320. The lead suture 220 is used to pull the fixation member 300 and the coupled tissue graft 200 through a tibia channel 16 and the femoral channel 14.

The intermediate portion 310 of the fixation member 300 includes a prominence 325 on a surface 330 of the intermediate portion 310. The prominence 325 is in the form of a pair of transversely extending tabs or bosses 340, 350 including a pair of keels or flanges 342, 344, and 352, 354, respectively, extending from leading and trailing edge portions of the tabs or bosses 340, 350. The tabs 340, 350 facilitate alignment of the tissue graft 200 with the fixation member 300 thus limiting any tendency of the fixation member 300 to rotate off-axis as it is being drawn through the bone tunnel. In addition, the tabs 340, 350 extend into or partially into the femoral tunnel when the fixation member 300 is positioned against the cortex at the opening to the tunnel, thereby assisting in centering the fixation member 300 on the bone. The continuous loop 210 of material can include a strip of polyethylene tape, suture material, or other suitable material.

Referring to FIGS. 2B and 2C, the fixation member 300 is an elongated member having the first end portion 305, the second end portion 320, and the intermediate portion 310 extending between and coupling the first and second end portions 305, 310. The first and second end portions 305, 320 define openings 308, 302, respectively, which are configured to receive the lead suture 220 and trailing suture 230, as noted above. The boss or tabs 340, 350 are formed at an outer edge of the intermediate portion 310 and extend transversely from the surface 330 of the intermediate portion 310. The boss or tabs 340, 350 include a pair of integrally-formed keels or flanges 342, 344, and 352, 354, respectively, axially extending from leading and trailing edge portions of the tabs or bosses 340, 350.

Figure 2D:
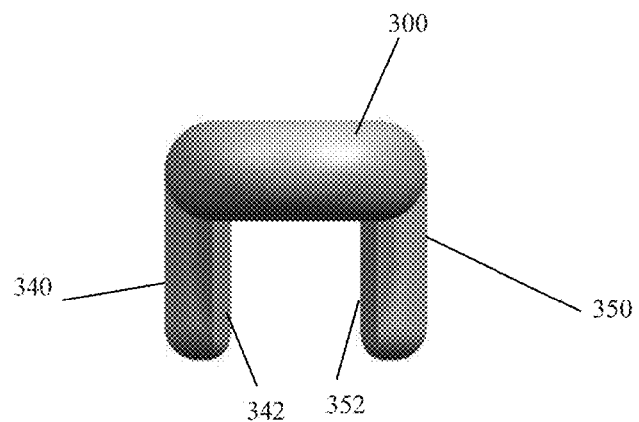
FIG. 2D is an end view of the fixation member of FIG. 2A

As can be seen in FIGS. 2C and 2D, the keels or flanges 342, 344, and 352, 354 are thinner as compared to their associated tabs or bosses 340, 350, and are generally formed integrally with their associated tabs or bosses 340, 350 via a tapered transition region 341, 351. In addition, the keels 342, 344, 352, and 354 include a tapered cutting edge 342a, 344a, 352a, and 354a, respectively, each of which seats or cuts into the cortical bone surrounding the tunnel 14 when the fixation member 300 is positioned against the cortex at the opening to the tunnel, which helps limit rotation of the fixation member 300. Referring to FIG. 2B, the keels 342, 344, 352, and 354 are tapered at an angle with respect to the surface 330 of the fixation member. This angle can be in the range of between about 95 degrees and about 160 degrees depending on the type of tissue graft tunnel and particular procedure.

An exemplary fixation member 300 has an overall length of between about 15 mm to about 25 mm, a width of between about 4 mm to about 9 mm, and a height of between about 1 mm to about 3 mm. The width of the boss is about 1 mm to about 2 mm and the thickness of the boss is about 1 mm. The length of the boss is such that it can fit in a tunnel of about 4 mm to 5 mm. The keel is angled at about 35 degrees to about 45 degrees from the bottom of the fixation member and is about 2 mm to about 3 mm in length.

While only certain implementations have been set forth, alternatives and modifications will be apparent from the above description to those skilled in the art. For example, rather than coupling the tissue graft indirectly to the fixation member, the tissue graft can be coupled directly to the fixation member by routing portions of the tissue graft through, for example, the two holes formed within the intermediate portion of the fixation member and between the boss/keel structures.

The leading and/or trailing ends can each be provided with one or more suture holes to facilitate positioning of the fixation member within the bone tunnel, and drawing the fixation member through the bone tunnel, and flipping the fixation member. The graft fixation member is formed from a biocompatible material such as titanium or PEEK, or a bioabsorbable material. The tissue graft may include autograft tissue, allograft tissue, or synthetic tissue. Additionally, instead of being positioned against the outer surface of the cortex at the opening to the femoral tunnel, the fixation member may be positioned inside the bone, thereby lying against the endosteal surface of the near cortex. As described above, suture material is used. However, other material that is strong enough to withstand pulling the fixation member/tissue graft combination through the bone tunnel could be used.

Although the present disclosure relates to graft fixation members and methods of use in a multiple-bundle technique, the graft fixation members and methods can be used in a single bone tunnel technique, advantageously with the bone tunnel positioned as tunnel 200b as shown in FIG. 1.

The aforementioned tissue graft fixation procedure may be applicable to other parts of the knee or other parts of the human body requiring tissue reconstruction.

These and other alternatives are considered equivalents and within the spirit and scope of this disclosure and the appended claims.

The invention claimed is:
1. A tissue graft fixation device comprising:
a body having an upper and lower surface, a first end portion, a second end portion, and an intermediate portion extending between the first and second end portions, the intermediate portion comprising at least two tabs extending transverse to the intermediate portion, the intermediate portion defining at least one hole located between the at least two tabs, and each of the at least two tabs comprising a keel extending perpendicular to the intermediate portion and including a cutting edge.

2. The device of claim 1 wherein the cutting edge of each keel of the at least two tabs is tapered at an angle relative to the lower surface of the body of the fixation device.

3. The device of claim 1 wherein the first end portion defines at least one hole and the second end portion defines at least one hole.

4. The device of claim 1 wherein each of the at least two tabs includes a pair of keels extending transverse to the intermediate portion, and each of the keels comprises a cutting edge.

5. The device of claim 4 wherein the cutting edge of each of the keels is tapered at an angle relative to the lower surface of the body of the fixation device.

6. The device of claim 1 wherein the intermediate portion defines at least two holes located between the at least two tabs.

7. The device of claim 1 wherein the at least two tabs are disposed along opposite outer edges of the intermediate portion of the device.

8. A tissue graft fixation device comprising:

a body having a first end portion, a second end portion, and an intermediate portion extending between the first and second end portions, the body configured for passage through a bone tunnel when oriented generally longitudinally with respect to the bone tunnel, the intermediate portion comprising two tabs extending transverse to the intermediate portion and the intermediate portion defining at least one hole located between the two tabs, the two tabs configured to at least partially fit through an opening and into the bone tunnel to limit translation of the device on a cortical bone surface, and each of the two tabs comprising two axially extending and tapered keels, each of the keels comprising a cutting edge configured to drive into a portion of the cortical bone surface to limit rotation of the device.

9. The device of claim 8 wherein the cutting edge of each keel is tapered at an angle relative to a lower surface of the body of the fixation device.

10. The device of claim 8 wherein the first end portion defines at least one hole and the second end portion defines at least one hole.

11. The device of claim 8 wherein the intermediate portion defines at least two holes located between the two tabs.

12. The device of claim 8 wherein the two tabs are disposed along opposite outer edges of the intermediate portion of the device.

13. The device of claim 1 wherein the at least two tabs further comprise a pair of coplanar opposed tabs extending from perpendicular to the keel and having cutting edges for cutting perpendicularly to a plane defined by the body.

* * * * *